(12) United States Patent
Suzuki et al.

(10) Patent No.: US 10,513,483 B2
(45) Date of Patent: Dec. 24, 2019

(54) METHOD OF PREPARING SUBSTITUTED BICYCLO[1.1.1] PENTANES

(71) Applicant: SPIROCHEM AG, Basel (CH)

(72) Inventors: Yoshikazu Suzuki, Glattbrugg (CH); Daniel Jimenez-Teja, Zurich (CH); Christophe Salomé, Herrlisheim près Colmar (FR); Thomas Fessard, Küsnacht (CH)

(73) Assignee: SPIROCHEM AG, Basel (CH)

( * ) Notice: Subject to any disclaimer, the term of this patent is extended or adjusted under 35 U.S.C. 154(b) by 0 days.

(21) Appl. No.: 16/085,163

(22) PCT Filed: Mar. 14, 2017

(86) PCT No.: PCT/EP2017/055979
§ 371 (c)(1),
(2) Date: Sep. 14, 2018

(87) PCT Pub. No.: WO2017/157932
PCT Pub. Date: Sep. 21, 2017

(65) Prior Publication Data
US 2019/0092714 A1    Mar. 28, 2019

(30) Foreign Application Priority Data
Mar. 14, 2016 (CH) .......................................... 330/16

(51) Int. Cl.
*C07C 67/343* (2006.01)
*C07C 45/68* (2006.01)
(Continued)

(52) U.S. Cl.
CPC .............. *C07C 67/343* (2013.01); *C07C 1/28* (2013.01); *C07C 45/68* (2013.01); *C07C 51/353* (2013.01); *C07C 67/31* (2013.01);
*C07C 67/313* (2013.01); *C07C 67/317* (2013.01); *C07C 227/18* (2013.01); *C07C 231/02* (2013.01); *C07C 231/12* (2013.01); *C07C 235/82* (2013.01);
(Continued)

(58) Field of Classification Search
None
See application file for complete search history.

(56) References Cited

U.S. PATENT DOCUMENTS 5,405,550 A * 4/1995 Michl .................... C07C 23/24
                                                          252/299.01

OTHER PUBLICATIONS

Sadovaya ("Unusual Directions in the Reactions of [1.1.1]Propellane with Sulfonyl Chlorides and Sulfuryl Chloride" Izvestiya Akademii Nauk SSSR, Seriya Khimicheskaya, vol. 10, 1990, p. 2451-2452) (Year: 1990).*

(Continued)

*Primary Examiner* — Amy C Bonaparte
(74) *Attorney, Agent, or Firm* — Pauley Erickson & Kottis

(57) ABSTRACT

A process for the preparation of a class of molecules, namely bicyclo[1.1.1]pentanes and derivatives thereof by reaction of [1.1.1]propellane with a variety of reagents under irradiation and/or in the presence of radical initiators to obtain bicyclo[1.1.1]pentanes asymmetrically substituted at position 1 and 3, which are useful as intermediates for the preparation of asymmetrically 1,3-disubstituted bicyclo[1.1.1]pentane derivatives and various physiologically active substances or materials containing these structures.

19 Claims, 4 Drawing Sheets

(51) Int. Cl.

| | |
|---|---|
| C07D 263/16 | (2006.01) |
| C07C 235/82 | (2006.01) |
| C07C 245/18 | (2006.01) |
| C07C 67/31 | (2006.01) |
| C07C 67/313 | (2006.01) |
| C07C 67/317 | (2006.01) |
| C07C 259/08 | (2006.01) |
| C07C 1/28 | (2006.01) |
| C07C 227/18 | (2006.01) |
| C07C 231/02 | (2006.01) |
| C07C 51/353 | (2006.01) |
| C07C 231/12 | (2006.01) |
| C07C 303/22 | (2006.01) |
| C07C 303/30 | (2006.01) |
| C07C 303/40 | (2006.01) |
| C07C 313/02 | (2006.01) |
| C07C 313/04 | (2006.01) |
| C07C 313/06 | (2006.01) |

(52) U.S. Cl.
CPC .......... *C07C 245/18* (2013.01); *C07C 259/08* (2013.01); *C07C 303/22* (2013.01); *C07C 303/30* (2013.01); *C07C 303/40* (2013.01); *C07C 313/02* (2013.01); *C07C 313/04* (2013.01); *C07C 313/06* (2013.01); *C07D 263/16* (2013.01); C07C 2531/12 (2013.01); C07C 2602/38 (2017.05); C07C 2603/62 (2017.05)

(56) References Cited

OTHER PUBLICATIONS

Ernest W. Della et al., "Synthesis of Some Bridgehead—Bridgehead-Disubstituted Bicyclo[1.1.1]pentanes," The Journal of Organic Chemistry, vol. 59, No. 11, pp. 2986-2996, Jun. 1, 1994.

J.D. Daniel Rehm et al., "A Facile Route to Bridgehead Disubstituted Bicyclo[1.1.1]pentanes Involving Palladium-Catalyzed Cross-Coupling Reactions," Cheminform, vol. 30, No. 51, pp. 2079-2085, Dec. 21, 1999.

Kenneth B. Wiberg, "Small-Ring Propellanes," Chemical Reviews, vol. 89, No. 5, pp. 975-983, Jul. 1, 1989.

Piotr Kaszynski et al., "A Practical Photochemical Synthesis of Bicyclo[1.1.1]pentane-1,3-dicarboxylic Acid," The Journal of Organic Chemistry, vol. 53, No. 19, pp. 4593-4594, Sep. 1, 1988.

Piotr Kaszynski et al., "Toward a Molecular-Size "Tinkertoy" Construction Set. Preparation of Terminally Functionalized [n]Staffanes from [1.1.1]Propellane," Journal of the American Chemical Society, vol. 114, No. 2, pp. 601-620, Jan. 1, 1992.

European Patent Office, English language version of the International Search Report, Form PCT/ISA/210 for International Application PCT/EP2017/055979, dated May 23, 2017 (2 pages).

European Patent Office, English language version of the Written Opinion of the International Searching Authority, Form PCT/ISA/237 for International Application PCT/EP2017/055979, dated May 23, 2017 (10 pages).

* cited by examiner

Fluoroquinolone
Antibacterial agent

JAK Inhibitor

γ-secretase inhibitor (A)

(B)

(A)

(B)

METHOD OF PREPARING SUBSTITUTED BICYCLO[1.1.1] PENTANES

FIELD OF THE INVENTION

The invention relates to a new and efficient process for the preparation of a class of molecules, namely bicyclo[1.1.1] pentanes and derivatives thereof by a one-step reaction of [1.1.1]propellane with a variety of reagents under irradiation and/or in the presence of radical initiators to obtain bicyclo [1.1.1]pentane intermediates asymmetrically substituted at position 1 and 3, which are useful for the preparation of various bicyclo[1.1.1]pentane derivatives and physiologically active substances or materials containing these.

BACKGROUND OF THE INVENTION

Bicyclo[1.1.1]pentanes and their derivatives are structural motifs in many physiologically active compounds and therefore are used as key intermediates in their preparation. It was shown that in a number of cases, active molecules containing these derivatives show useful physico-chemical properties and that their use is sometimes superior to more standard fragments such as aromatic or lipophilic groups, making them potential bioisosters for phenyl or tert-butyl groups as postulated and/or demonstrated in the literature (e.g. M. R. Barbachyn et al. *Bioorg. Med. Chem. Lett.* 1993, 3, 671-676, A. F. Stepan et al. *J. Med. Chem.* 2012, 55, 3414-3424, K. D. Bunker et al. *Org. Lett.* 2011, 13, 4746-4748 and Y. L. Goh et al. *Org. Lett.* 2014, 16, 1884-1887).

Bicyclo[1.1.1]pentanes have been used as intermediates in the preparation of various compounds with different areas of application. Thus, the properties displayed by compounds containing bicyclo[1.1.1]pentanes are not limited to a particular medical indication (see for example FIG. 1 describing several physiologically active compounds that have been reported to benefit from the properties of the bicyclo[1.1.1] pentanes, such as fluoroquinolone antibiotics, JAK inhibitors or gamma-secretase inhibitors).

There is therefore an increasing interest in the area of life science as well as material sciences to access the most diverse set of bicyclo[1.1.1]pentane derivatives in large quantities in a time and cost efficient manner. However, the current process to make bicyclo[1.1.1]pentane derivatives is still tedious and requires several steps, especially for the synthesis of asymmetrically substituted derivatives, and often requires toxic reagents. To date two main approaches are known to access bicyclo[1.1.1]pentanes:

The first one requires the preparation of bicyclo[1.1.0] butanes followed by cyclopropanation with a carbene (:CCl2) and dechlorination, as reported by Applequist et al. *J. Org. Chem.* 1982, 4985-4995 (FIG. 2A). However, this synthesis uses toxic and/or expensive reagents and presents moderate yields.

The second approach is the most described synthesis in the prior art (*Org. Synth.* 1998, 75, 98; *Org. Synth.* 2000, 77, 249) in which the central bond of [1.1.1]propellane is reacted with a variety of reagents to form 1,3-disubstituted bicyclo[1.1.1]pentanes.

The scope of reagents and reactions mainly delivers symmetrical bicyclo[1.1.1]pentane derivatives, or asymmetrically substituted derivatives that are limited to substituents unsuitable for further derivatization. Furthermore, the yields are usually low to moderate and suffer from contamination with a number of by-products, principally due to polymerization and dimerization.

The synthesis of asymmetrical derivatives is in particular challenging and obtained products are usually in form of mixtures with by-products, regio-isomers or polymers.

One particular method (P. Kaszyncki, and J. Michl, *J. Org. Chem.* 1988, 53, 4594-4596) to access synthetically useful intermediates such as 1,3-disubstituted monoacid-monoesters consists in treating [1.1.1]propellane with buta-2,3-dione under irradiation to give the diketone intermediate (FIG. 2B). Subsequent haloform reaction, followed by diester formation and mono-saponification afforded the desymmetrized product. However, a total of 6 reaction steps are required with an overall yield varying between 20% and 40%, associated with problems of reproducibility and the need for repeated purifications at each step make this route very difficult in particular to perform on large scale.

Therefore, there is a need for a synthetically efficient route that could overcome the disadvantages of the methods in the prior art, which is also compatible with large-scale production using common reagents and minimal need for purification.

Applicants have now found a new, efficient, selective and versatile method for synthesizing a wide range of asymmetrically 1,3-disubstituted bicyclo[1.1.1]pentane intermediates and symmetrically and asymmetrically mono- and 1,3-disubstituted bicyclo[1.1.1]pentane derivatives thereof.

SUMMARY OF THE INVENTION

The present invention provides an improved method for the preparation of asymmetrically 1,3-disubstituted bicyclo [1.1.1]pentane intermediates in a highly efficient manner by using a one-step photochemical and/or radical reaction (in a batch or flow system). The obtained bicyclo[1.1.1]pentane intermediates are suitable for derivatization using any standard reaction disclosed in the prior art to obtain symmetrically and asymmetrically mono- and 1,3-disubstituted bicyclo[1.1.1]pentane derivatives.

More specifically, the present invention provides in one aspect a one-step process (hereinafter also called reaction step B) for producing an asymmetrically substituted compound of formula I, wherein

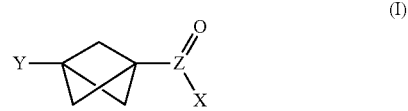
(I)

comprising the step of reacting [1.1.1]propellane of formula II

(II)

with a compound of formula III, wherein

(III)

Z is C, or S or S(=O)
Y is $R_1$—C(=O)—, $R_1$OC(=O)—, $CH_2F$—, $CHF_2$—, $CF_3$—, $C_2F_5$—, $C_3F_7$—, —CN, $R_1R_2NC$(=O)—, $R_1SC$(=O), $R_1R_2N$—, $NO_2$, $CH$(=$NOR_1$), wherein $R_1$ and $R_2$ are independently of each other H, saturated linear or branched —(C$_1$-C$_{20}$)alkyl, aryl or form together a cycle,
X is halogen, OR$_1$, R$_1$, NR$_1$R$_2$, wherein R$_1$ and R$_2$ are independently of each other H, saturated linear or branched —(C$_1$-C$_{20}$)alkyl, aryl or form together a cycle.

In specific embodiments the method of the invention is directed towards a one-step process wherein X is halogen, preferably Cl for producing a compound of formula Ia, preferably Ib

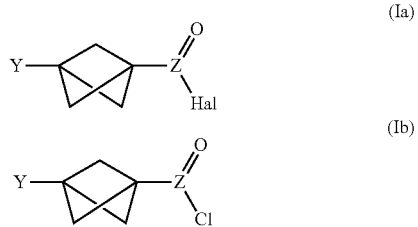

In another aspect the present invention provides the use of the obtained compound of formula I, preferably formula Ia, more preferably Ib, as an intermediate without further purification in subsequent derivatization reactions. Thus, in a specific embodiment the one step process for producing a compound of formula I (or Ia or Ib) is followed by the step (hereinafter also called reaction step C) of reacting the obtained compound of formula I, preferably formula Ia or Ib, with a nucleophile, to obtain a compound of formula V

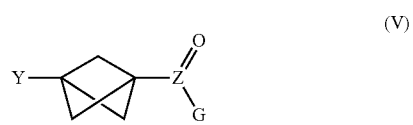

wherein
Z is C, or S or S(=O),
Y is R$_1$—C(=O)—, R$_1$OC(=O)—, CH$_2$F—, CHF$_2$—, CF$_3$—, C$_2$F$_5$—, C$_3$F$_7$—, —CN, R$_1$R$_2$NC(=O)—, R$_1$SC (=O), R$_1$R$_2$N—, NO$_2$, CH(=NOR$_1$), wherein R$_1$ and R$_2$ are independently of each other H, saturated linear or branched —(C$_1$-C$_{20}$)alkyl, aryl or form together a cycle, and
G is —OR$_1$, —SR$_1$, —NR$_1$R$_2$, —N$_3$, —NH—NHR$_1$, —NH—OR$_1$, —C(=N$_2$)H, —O—(N-2-thiopyridone), R$_1$, —O(C(=O)R$_1$, wherein R$_1$ and R$_2$ are independently of each other H, saturated linear or branched —(C$_1$-C$_{20}$)alkyl, aryl or form together a cycle.

In a further embodiment the [1.1.1]propellane of formula II is obtained by reaction of a tetrahalide of formula IV with 2 or more equivalents of an alkyl or aryl lithium at temperatures below 0° C. (hereinafter also called reaction step A).

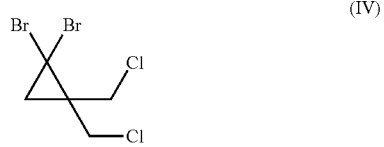

In a specific embodiment the reaction steps B and C to obtain a compound of Formula V from a compound of Formula II (via the intermediate of Formula I, preferably Formula Ia or Ib) are performed (a) in a batch system or (b) in a flow system.

In another specific embodiment the reaction steps A and B to obtain a compound of Formula I, preferably Formula Ia or Ib, from a compound of Formula IV are performed (a) in a batch system or (b) in a flow system.

In yet another specific embodiment the reaction steps A and B and C to obtain a compound of Formula V from a compound of Formula IV (via the intermediate of Formula I, preferably Formula Ia or Ib) are performed (a) in a batch system and/or (b) in a flow system.

In a further embodiment the step of reacting [1.1.1] propellane of formula II with a compound of formula III is carried out under irradiation and/or in the presence of a radical initiator In one embodiment, the nucleophile reacting with a compound of formula I (or Ia or Ib) is water, such as an aqueous solution of an organic or inorganic base to form products of formula (Va), wherein

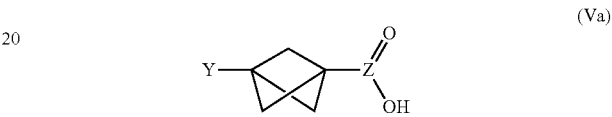

Z represents C, or S or S(=O)
resents R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—, R$_1$SC (=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, aryl, or form together a cycle.

In another embodiment, the nucleophile reacting with a compound of formula I (or Ia or Ib) is an alcohol or N-hydroxy-2-thiopyridone (or its anion) of formula R$_3$—OH to form products of Formula (Vb), wherein

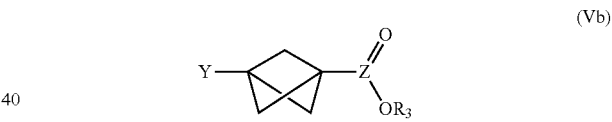

Z represents C, or S or S(=O)
Y represents R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, aryl, or form together a cycle and R$_3$ is H, saturated linear or branched —(C$_1$-C$_{20}$)alkyl, aryl or —N-2-thiopyridone.

In another embodiment, the nucleophile reacting with a compound of formula I (or Ia or Ib) is an amine of formula HNR$_1$R$_2$ to form products of Formula (Vc), wherein

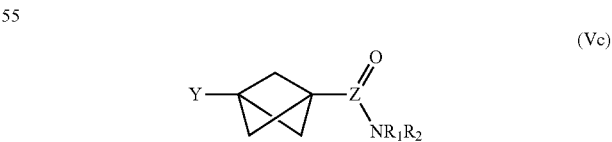

Z represents C, or S or S(=O)
Y represents R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, aryl, or form together a cycle.

In another embodiment, the nucleophile reacting with a compound of formula I (or Ia or Ib) is an azide (—N$_3$), ammonia, a hydrazine (H$_2$N—NHR$_1$), an hydroxylamine (H$_2$N—OR$_1$) or a diazo compound (R$_4$—CH=N$_2$) to form products of Formula (Vd-Vh), wherein

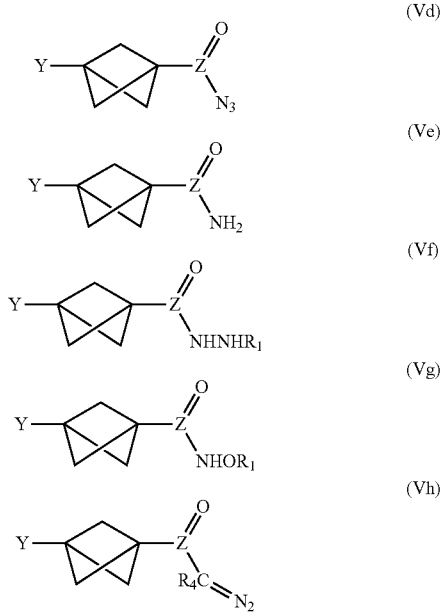

Z represents C, or S or S(=O)
Y represents R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, aryl or form together a cycle
R$_4$ represents H, saturated or unsaturated linear or branched —(C$_1$-C$_{20}$)alkyl, TMS, aryl or form together a cycle.

In another embodiment, Z is C, X is Cl and the acid chloride of formula III formed is coupled under transition-metal catalysis with a coupling partner, a coupling partner being an alkali metal organyl or an alkaline earth metal organyl (MR$_1$, wherein M is Li, Na or Mg), a stannane (R$_1$Sn(R$_2$)$_3$), a cuprate [R$_1$CuR$_1$]$^-$ or [R$_1$CuCN]$^-$) an organozinc compound (R$_1$ZnQ, or R$_1$ZnR$_1$, wherein Q is halogen), an organobismuth compound ((R$_1$)$_3$Bi), a boronic acid R$_1$B(OH)$_2$, a boronic ester R$_1$B(OR$_2$)$_2$ or a potassium trifluoroborate R$_1$BF$_3$K, wherein R$_1$ and R$_2$ are independently of each other —(C$_1$-C$_{20}$)alkyl, aryl or heteroaryl to form products of formula Vi wherein

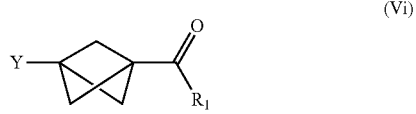

Z represents C
Y represents R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, aryl or form together a cycle.

In a preferred embodiment Z is C, in another preferred embodiment Z is S, in a further preferred embodiment Z is S(=O).

DETAILED DESCRIPTION OF THE INVENTION

Figure 1:
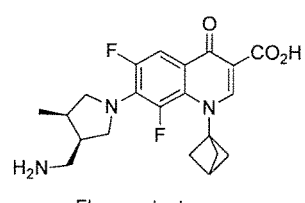
FIG. 1. Physiologically active compounds containing bicyclo[1.1.1]pentane units, such as fluoroquinolone antibiotics, JAK inhibitors or gamma-secretase inhibitors.
Figure 1:
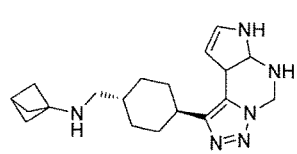
Figure 1:
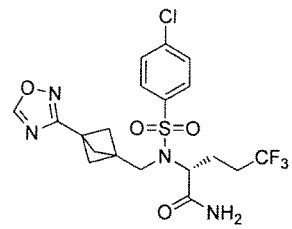
Figure 2:
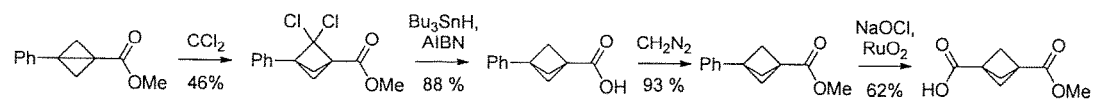
FIG. 2 (A) Synthesis of bicyclo[1.1.1]pentanes by first preparing bicyclo[1.1.0]butanes followed by cyclopropanation with a carbene:CCl2 and dechlorination (Applequist et al. *J. Org. Chem.* 1982, 4985-4995). (B) Synthesis of bicyclo[1.1.1]pentanes by treating [1.1.1]propellane with buta-2,3-dione under irradiation to give the diketone intermediate, followed by a haloform reaction, and subsequent di-ester formation and mono-saponification (P. Kaszyncki, and J. Michl, *J. Org. Chem.* 1988, 53, 4594-4596)
Figure 2:
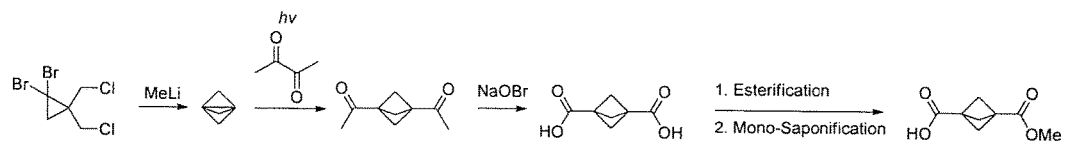
Figure 3:
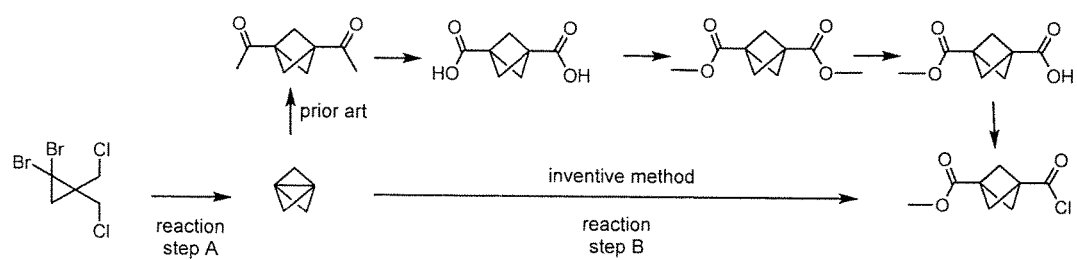
FIG. 3 (A) Schematic comparison of synthesis of asymmetric acid chlorides according to prior art methods and the methods of the present invention FIG. 3 (B) Reactivity of bicyclo[1.1.1]pentanes as prepared by the methods of the invention (reaction step C)
Figure 3:
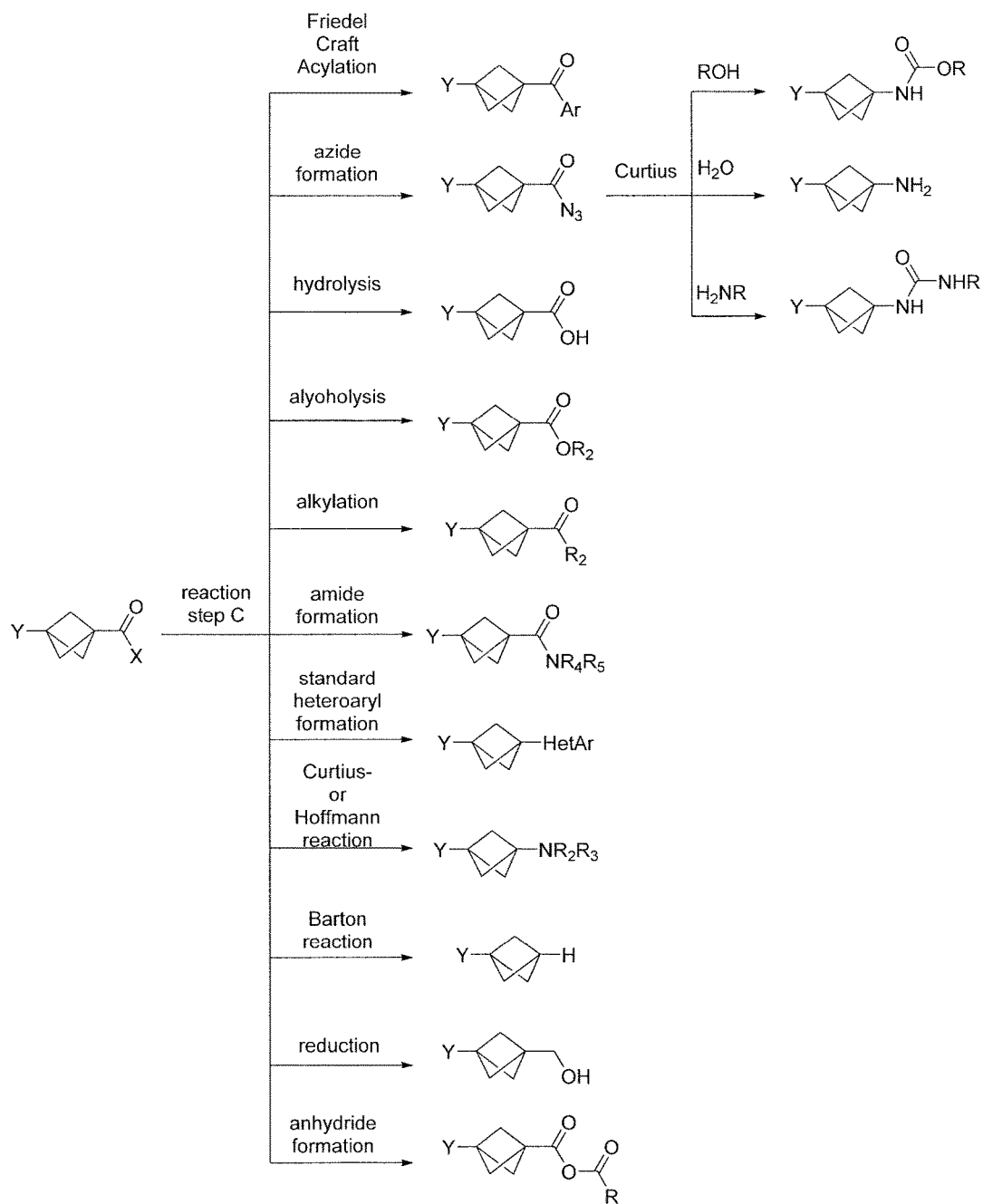

The present invention provides an improved method for the one-step preparation of asymmetrically 1,3-disubstituted bicyclo[1.1.1]pentane intermediates in a highly efficient manner by using a photochemical and/or radical reaction. The obtained bicyclo[1.1.1]pentanes are reactive intermediates, which are suitable for use in any standard derivatization reaction disclosed in the prior art to obtain asymmetrically or symmetrically mono- and 1,3-disubstituted bicyclo[1.1.1]pentane derivatives in a batch or flow system.

The term "bicyclo[1.1.1]pentane intermediate(s)" is used for asymmetrically 1,3-disubstituted compounds of formula I (or an acid halide of formula Ia or an acid chloride of formula Ib), while the term "bicyclo[1.1.1]pentane derivatives" is used for asymmetrically or symmetrically mono- and 1,3-disubstituted compounds of formula V (or formula Va-Vi), which are obtained by reacting the reactive bicyclo[1.1.1]pentane intermediates with various nucleophiles.

The term "asymmetrically" as used herein refers to compounds of formula I (or Ia or Ib), wherein the two ring substituents of a bicyclo[1.1.1]pentane intermediate (i.e. group Y and group —Z(=O)X) are not identical.

As used herein, the term "alkyl" refers to a fully saturated linear or branched hydrocarbon moiety having 1 to 20 carbon atoms, wherein the alkyl radical may be optionally substituted independently with one or more substituents described herein. Unless otherwise provided, alkyl refers to hydrocarbon moieties having 1 to 16 carbon atoms, 1 to 10 carbon atoms, 1 to 8 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

The term "carbocyclyl" or "carbocycle" refers to a saturated or partially unsaturated, cyclic or branched cyclic group, having one, two or more rings, preferably one ring formed by a skeleton that contains from 3 to 14 carbon atoms, preferably from five or six to ten carbon atoms, for example cyclopropyl, cyclobutyl, cyclopentyl, cyclohexyl, tetralin, cyclopentenyl or cyclohex-2-enyl groups. The unsaturated carbocyclic groups contain preferably one or two double and/or triple bonds.

As used herein, the term "heterocyclyl" or "heterocycle" refers to a 5 to 15 membered saturated non-aromatic ring or multiple condensed ring system, e.g. a 4-, 5-, 6-, or 7-membered monocyclic, 6-, 7-, 8-, 9-, 10-, 11-, or 12-membered bicyclic or 10-, 11-, 12-, 13-, 14- or 15-membered tricyclic ring system, having from 2 to 14, preferably from 2 to 6 carbon atoms, and from 1 to 8, preferably from 1 to 4 heteroatoms, selected from nitrogen, sulfur, phosphorus, and/or oxygen within the ring. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathioiane, dithiolane, 1,3-dioxane, 1, 3-dithiane, oxathiane and thiomorpholine. A heterocyclic group may be optionally substituted with 1 to 5 substituents independently selected from the groups referred to hereinafter.

As used herein, the term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). Preferably, aryl groups are from 6 to 10 membered ring systems and include phenyl, fluorenyl, naphthyl, anthryl, and the like. An aryl group may be optionally substituted with 1 to 5 substituents independently selected from the groups referred to hereinafter.

As used herein, the term "heteroaryl" refers to a 5 to 20 membered monocyclic- or bicyclic- or tricyclic-aromatic ring system, having 1 to 10 heteroatoms selected from N, O or S. Typically, the heteroaryl is a 5 to 10 membered ring system (e.g., 5 to 7 membered monocycle or an 8 to 10 membered bicycle) or a 5 to 7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl. A heteroaryl group may be optionally substituted with 1 to 5 substituents independently selected from the groups referred to hereinafter.

As used herein, the term "alkylaryl" refers to combinations of —($C_1$-$C_5$)alkyl and ($C_6$-$C_{12}$)aryl groups, optionally substituted by one or more selected from halogen or methoxy groups. Examples of alkylaryl groups include benzyl, paramethoxybenzyl, metacholorobenzyl groups.

As used herein, the term "alkylheteroaryl" refers to combinations of —($C_1$-$C_5$)alkyl and ($C_6$-$C_{12}$)heteroaryl groups containing one to three heteroatoms selected from N, O or S, optionally substituted by one or more selected from halogen or methoxy groups.

As used herein, the term "halogen" or "hal" with respect to group X refers to fluoro, chloro, bromo, and iodo, preferably fluoro, chloro, bromo, more preferably chloro; and "halogen" or "hal" with respect to group Q refers to fluoro, chloro, bromo, and iodo.

As used herein, the term "optionally substituted" with respect to the groups defined herein refers, unless otherwise specified, to a group that is unsubstituted or is substituted by one or more, such as 1 to 5, preferably 1, 2, 3 or 4, suitable non-hydrogen substituents, each of which is independently selected from the group consisting of alkyl, alkenyl, alkynyl, hal, -oxo (=O), —$OR_1$, —$NR_1R_2$, —$SR_1$, nitro, cyano, —$COR_1$, —$COOR_1$, —$CONR_1R_2$, cycloalkyl, heterocyclyl, aryl, heteroaryl as defined herein, wherein $R_1$ and $R_2$ are independently of each other H, saturated linear or branched —($C_1$-$C_{20}$)alkyl, wherein one or two non-adjacent $CH_2$ groups may be replaced by —O—, —CH=CH—, —CO—, —OCO—, —COO—, —NCO—, —CON—, in such a way that O atoms are not linked directly to one another.

Groups $R_1$ and $R_2$ are independently of each other H, saturated linear or branched —($C_1$-$C_{20}$)alkyl, aryl or form together a cycle. In specific embodiments, $R_1$ and $R_2$ are independently of each other H, saturated linear or branched —($C_1$-$C_{20}$)alkyl, preferably —($C_1$-$C_{12}$)alkyl, more preferably —($C_1$-$C_8$)alkyl, wherein one or two non-adjacent $CH_2$ groups may be replaced by —O—, —CH=CH—, —CO—, —OCO—, —COO—, —NCO—, —CON—, in such a way that O atoms are not linked directly to one another; preferably —($C_1$-$C_8$)alkyl, wherein one or two non-adjacent $CH_2$ groups may be replaced by —O—, —CH=CH—, —CO—, —OCO—, —COO—. The terms "alkyl" and "aryl" in connection with groups $R_1$, $R_2$, $R_3$ and $R_4$ are defined as hereinabove, the term "cycle" is defined as hereinabove by carbocyclyl, heterocyclyl, aryl and heteroaryl. In a specific embodiment, "alkyl" includes methyl, ethyl, propyl, butyl, pentyl, tert-butyl, "aryl" includes phenyl, benzyl, and "cycle" includes cyclopentyl, cyclohexyl.

As used herein, the term "one pot" process refers to two or more consecutive reactions, which are carried out without isolating and/or purifying the respective intermediates, typically in a single reaction vessel. One-pot-processes are amenable to be used in continuous process reactors, or continuous flow reactors, wherein fresh reactants are continuously added to the reactor and the reaction products are continuously removed.

As used herein the term "leaving group" or "LG" is readily understood by those skilled in the art and is typically any group or atom that enhances the electrophilicity of the atom to which it is attached for easy displacement. Preferred leaving groups are halogen atoms such as chloride, bromide, iodide or sulfonyl groups such as mesylate, tosylate, perfluorosulfonylate. When the leaving group is attached to a carbonyl group, it can be a halogen or sulfonyl group as defined above or an ester so that the carbonyl group is activated as an anhydride.

The term "nucleophile" is readily understood by a person skilled in the art as a chemical species which donates an electron pair to an electrophile to form a chemical bond. Examples of nucleophiles include uncharged compounds such as amines, enamines, hydrazines, enols, mercaptans, alcohols, carboxylic acids, diazo compounds and azides, and charged moieties such as alkoxides, carboxylates, thiolates, carbanions, metallated amines (e.g., amine anions, for example, sodamide), and a variety of organic and inorganic anions (for example $NaN_3$). Preferred nucleophiles for use in the present invention include aliphatic and aromatic alcohols of formula $HOR_1$, mercaptans of formula $HSR_1$, azides —$N_3$, ammonia ($H_3N$), amines of formula $HNR_1R_2$, hydrazines of formula $H_2N$—$NHR_1$, hydroxylamines of formula $H_2N$—$OR_1$, diazomethanes of formula $R_4$—HC(=$N_2$), N-hydroxy-2-thiopyridone (or anions thereof).

The term "coupling partner" is understood as a chemical species comprising at least one hydrocarbon fragment and is able to undergo a transition metal catalyzed coupling reaction forming a new carbon-carbon bond. Examples of coupling partners include organohalides, boronic acids, boronic esters, potassium trifluoroborates, transition metal organyls such as stannanes, cuprates, organozinc compounds or organobismuth compounds or alkali or alkaline earth organyls, more specifically alkali metal organyl or an alkaline earth metal organyl ($MR_1$, wherein M is Li, Na or Mg), a stannane ($R_1Sn(R_2)_3$), a cuprate [$R_1CuR_1$]⁻ or [$R_1CuCN$⁻]) an organozinc compound ($R_1ZnQ$, or $R_1ZnR_1$, wherein Q is halogen), an organobismuth compound (($R_1)_3Bi$), a boronic acid $R_1B(OH)_2$, a boronic ester $R_1B(OR_2)_2$ or a potassium trifluoroborate $R_1BF_3K$.

As used herein the term "radical initiator" is defined as a substance that can produce radical species under mild conditions and promote radical reactions. These substances generally possess weak bonds-bonds that have small bond dissociation energies. Typical examples are halogen molecules, azo compounds, and organic and inorganic peroxides. Radical initiators can be used in catalytic amounts, in stoichiometric amount or in excess, preferably in catalytic amounts.

The term "one-step" as used herein with respect to a specific reaction or method steps means a direct conversion of the starting material(s) to the respective product (for example direct conversion of compounds of formula II and III to a compound of formula I or V or conversion of compounds of formula IV to a compound of formula I or V via the compound of formula II) without the formation of an intermediate step.

The term "flow" as used herein in the context of a "flow reaction", a "flow process" applies to chemical reactions run in a continuously flowing stream rather than in batch production. Pumps or sur-pressures are used to move a fluid (liquid, solutions or suspensions) into a tube, and where tubes containing fluid join one another, the fluids contact one another. If these fluids are composed of or contain molecules that can react together, a reaction takes place. The reaction may need to be catalyzed or initiated by external factors such as temperature or irradiation.

As used herein the term "flow system" refers to the equipment, vessels, tubing used to perform a flow reaction as described above.

As used herein, the term "continuous flow" refers to a series of transformations where the product of a reaction performed in flow in a flow system is directly transferred to another flow system to undergo another reaction.

As used herein, the term "batch", "batch system" or "batch reaction" refers to chemical transformations performed in a vessel using techniques that are standard for those skilled in the art.

Referring to a reaction sequence such as reaction steps A, B and C being performed in a "batch system and/or flow system" means that any combination of batch and flow system can be used, more specifically (i) reaction steps A, B, C can be run in batch, or (ii) reaction step A can be run in batch and reaction steps B, C in flow, or (iii) reaction steps A, B can be run in flow and reaction step C in batch or (iv) reaction steps A, B, C can be run in flow.

The photoreactor for a batch system consists in a lamp, a jacketed immersion well, a cold finger condenser, a reaction vessel, a cooling bath, and a magnetic-stirrer device. The lamp can be a low-pressure, medium-pressure or high pressure mercury lamp, LED lamp, a UVC lamp or an incandescent lamp (for instance a tungsten lamp). The wavelength suitable for such transformation can be in the visible and/or UV spectra. An immersion well is used for cooling down the lamp is made by double-walled quartz or borosilicate glass being transparent to UV light and thus transmitting light with wavelengths at a wide, in particular wavelengths as low as 200 nm, more specifically wavelengths between 200 nm-400 nm. A typical reaction set-up may include e.g. a reaction vessel, which is a multi-necked flask or reactor. The cold finger condenser works as a trap of volatile organic compounds and is installed in one of the 4 neck of the reaction vessel. It is also possible to use several lamps equipped with suitable cooling systems positioned around or in the reaction vessel to maximize irradiation.

The photoreactor for a flow system is constructed by wrapping 1, 2, 3 or more layers of tubing around the jacketed immersion well containing a lamp and cooled down with water or any other solvent. The photoreactor for flow system is wrapped in aluminium foil or any reflective material in order to minimize light loss, and cooled with a cooling bath. The reaction solutions are pumped through the reactor using a pump, or a sur-pressure in the flask containing the solution, at controlled flow rates via mixing device and a back pressure regulator. The lamp can be a low-pressure, medium-pressure or high pressure mercury lamp, LED lamp, a UVC lamp or an incandescent lamp (for instance a tungsten lamp). The wavelength suitable for such transformation can be in the visible and/or UV spectra. The immersion well for cooling down the lamp is made by double-walled quartz or borosilicate glass. The tubing around the jacketed immersion well can be a Fluorinated Ethylene Propylene (FEP) tubing, a polytetrafluoroethylene (PTFE) tubing, or other tubing allowing external light to irradiate the content of the tubing. The size of tubing can be ¹⁄₁₆", ⅛", ¼", ³⁄₁₆", etc. The pump can be a HPLC pump, a peristaltic pump, a syringe pump, etc. The mixing device can be for example a Tefzel® (ETFE) Tee, PEEK Tee, Steel Tee or others.

The present invention provides an improved method for the one-step preparation of asymmetrically 1,3-di-substituted bicyclo[1.1.1]pentane intermediates of Formula I

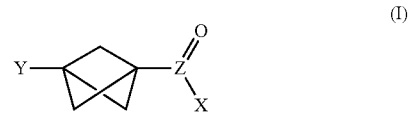
(I)

comprising the step of reacting [1.1.1]propellane of Formula II

(II)

with an appropriate compound of Formula III

(III)

wherein
Z is C, or S or S(=O)
Y is $R_1$—C(=O)—, $R_1$OC(=O)—, —$CH_2F$, —$CHF_2$, —$CF_3$, —$C_2F_5$, —$C_3F_7$, —CN, $R_1R_2$NC(=O)—, RSC(=O)—, $R_1R_2$N—, —$NO_2$, —CH(=$NOR_1$), wherein $R_1$ and $R_2$ are independently of each other H, saturated linear or branched —($C_1$-$C_{20}$)alkyl, aryl or form together a cycle.

X is halogen, —$OR_1$, —$NR_1R_2$, wherein $R_1$ and $R_2$ are independently of each other H, saturated linear or branched —($C_1$-$C_{20}$)alkyl, aryl or form together a cycle.

Illustrative examples of a compound of Formula III include, but are not limited to, methyl 2-chloro-2-oxoacetate or ethyl chlorooxoacetate or 2-oxo-2-phenylacetyl chloride or methyl 2,2,2-trifluoroacetate or trifluoroacetyl chloride or 1,1,1-trifluoroacetone or 2,3-hexadione or 3,4-hexadione or 1-(3-methylphenyl)-2-phenyl-1,2-ethanedione or 1,2-bis(4-chlorophenyl)-1,2-ethanedione or any other in a photochemical reaction in batch or in a flow system.

Amounts of reactant undergoing homolytic or heterolytic cleavage can be sub-stoichiometric amount, stoichiometric amount or in excess, preferably in a range between 0.5 and 3 equivalents compared to [1.1.1]propellane.

In preferred embodiments, X is halogen, more preferably Cl.

Thus, in specific embodiments the method of the invention is directed towards a one-step process wherein X is halogen, preferably Cl for producing a compound of formula Ia, preferably Ib

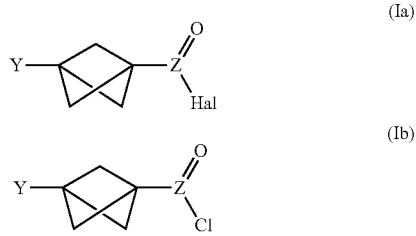

In another aspect the present invention provides the use of the obtained compound of formula I, preferably formula Ia, more preferably Ib, as an intermediate without further purification in subsequent derivatization reactions. Thus, in a specific embodiment the one step process for producing a compound of formula I (or Ia or Ib) is followed by the step (hereinafter also called reaction step C) of reacting the obtained compound of formula I, preferably formula Ia or Ib, with a nucleophile, to obtain a compound of formula V

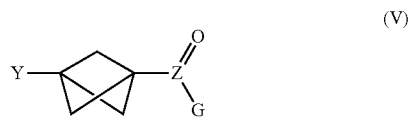

wherein
Z is C, or S or S(=O),
Y is $R_1$—C(=O)—, $R_1$OC(=O)—, $CH_2F$—, $CHF_2$—, $CF_3$—, $C_2F_5$—, $C_3F_7$—, —CN, $R_1R_2$NC(=O)—, $R_1$SC(=O), $R_1R_2$N—, $NO_2$, CH(=$NOR_1$), wherein $R_1$ and $R_2$ are independently of each other H, saturated linear or branched —($C_1$-$C_{20}$)alkyl, aryl or form together a cycle, and
G is —$OR_1$, —$SR_1$, —$NR_1R_2$, —$N_3$, —NH—$NHR_1$, —NH—$OR_1$, —C(=$N_2$)H, —O—(N-2-thiopyridone), $R_1$, —O(C(=O)$R_1$, wherein $R_1$ and $R_2$ are independently of each other H, saturated linear or branched —($C_1$-$C_{20}$)alkyl, aryl or form together a cycle.

In other embodiments the preparation of [1.1.1]propellane (reaction step A) for further use in the one-step method of the invention, is as follows:

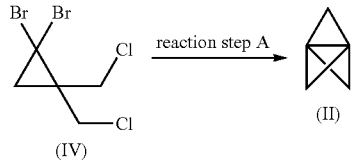

In a particular embodiment, [1.1.1]propellane is obtained from 1,1-dibromo-2,2-bis(chloromethyl)cyclopropane, preferably through a halogen-lithium exchange of bromine atoms with a suitable organolithium species such as MeLi, EtLi, PrLi, iPrLi, nBuLi, sec-Buli, tBuLi or an aromatic-Lithium species such as PhLi or the like. In a preferred embodiment the organolithium species is added (preferably as a solution) in a batch system to a reactor containing 1,1-dibromo-2,2-bis(chloromethyl)cyclopropane as a suspension or solution in a suitable solvent. Solvents of choice for 1,1-dibromo-2,2-bis(chloromethyl)cyclopropane include alkanes (pentane, hexane, heptane, cyclohexane, petroleum ether) aromatic solvents (benzene, toluene, cymene) or ethers (diethyl ether, diisopropyl ether, TBME, THF, MeTHF). Temperatures of addition are between −80° C. and 0° C., preferably between −60° C. and −20° C. The reaction is then left at a temperature ranging from −20° C. and 50° C., preferably between 0° C. and 30° C. Reactions times range from 1 h and 12 h, preferably between 1 h and 6 h.

In another embodiment, the solution of organolithium species is pumped or pushed using a sur-pressure into a flow system where it is mixed to a solution or suspension of 1,1-dibromo-2,2-bis(chloromethyl)cyclopropane also added using a pump or sur-pressure.

In one embodiment, the obtained [1.1.1]propellane is either distilled from the reactor if the solvent of choice is a low-boiling solvent or co-distilled from the reactor with the reaction solvent if the solvent is a high-boiling solvent. The obtained [1.1.1]propellane (or solution of [1.1.1]propellane) is condensed using a cooling system at a range between −196° C. to 0° C., preferably between −80° C. and −20° C.

In another embodiment, the reaction mixture is cooled to a temperature ranging from −80° C. to 0° C., preferably between −60° C. to 20° C. and quenched with an aqueous solution of a base, preferably an inorganic base, before being extracted at a pH ranging from 1 to 10 with an appropriate solvent.

In another embodiment, the reaction mixture is filtered through a pad of unreactive material such as silica or celite or glass beads or any sort of filter.

In yet another embodiment, the solution of distilled or crude or filtered [1.1.1]propellane is reacted directly in the next batch reaction with or without further dilution.

In yet another embodiment, the solution of distilled or crude or filtered [1.1.1]propellane is pumped directly in a flow reactor, with or without dilution.

In one embodiment Z represents C and Y, X are as defined above; or Z represents S and Y, X are as defined above; or Z represents S(=O) and Y, X are as defined above.

In another embodiment X represents Halogen, preferably Cl, and Y, Z are as defined above; or X represents $OR_1$ and Y, Z are as defined above; or X represents $R_1$ and Y, Z are as defined above; or X represents $NR_1R_2$ and Y, Z are as defined above.

In a specific embodiment, Z represents C, Y represents R₁—C(=O)—, R₁OC(=O)—, —CH₂F, —CHF₂, —CF₃, —C₂F₅, —C₃F₇, —CN, R₁R₂NC(=O)—, R₁SC(=O)—, R₁R₂N—, —NO₂, —CH(=NOR₁), wherein R₁ and R₂ are independently of each other H, saturated linear or branched —(C₁-C₂₀)alkyl, aryl or form together a cycle and X represents halogen, —OR₁, —NR₁R₂, wherein R₁ and R₂ are independently of each other H, saturated linear or branched —(C₁-C₂₀)alkyl, aryl or form together a cycle, preferably halogen, more preferably chloride.

In another specific embodiment, Z represents S(=O), Y represents R₁—C(=O)—, R₁OC(=O)—, —CH₂F, —CHF₂, —CF₃, —C₂F₅, —C₃F₇, —CN, R₁R₂NC(=O)—, R₁SC(=O)—, R₁R₂N—, —NO₂, —CH(=NOR₁), wherein R₁ and R₂ are independently of each other H, saturated linear or branched —(C₁-C₂₀)alkyl, aryl or form together a cycle, and X represents halogen, —OR₁, —NR₁R₂, wherein R₁ and R₂ are independently of each other H, saturated linear or branched —(C₁-C₂₀)alkyl, aryl or form together a cycle, preferably halogen, more preferably chloride. In specific embodiments (which applies to all of the above combinations) Y is R₁—C(=O)—, R₁OC(=O)—, —CH₂F, —CHF₂, —CF₃, —CN, R₁R₂NC(=O)—, R₁SC(=O)—, R₁R₂N—, preferably R₁—C(=O)—, R₁OC(=O)—, R₁R₂NC(=O)—, R₁SC(=O)—, R₁R₂N—, more preferably R₁—C(=O)— or R₁OC(=O)— or R₁R₂NC(=O)— or R₁R₂N—.

In specific embodiments (which applies to all of the above combinations) R₁ and R₂ are independently of each other H In one embodiment, the reaction proceeds at a temperature range of −50° C. to RT, preferably −40° C. to 0° C.

In another embodiment, the concentration of the reaction is in a range of 0.01M to 2M.

In another embodiment, the reaction time is between 1 min to 12 h.

In another embodiment, the reaction is performed in a batch reactor equipped with a irradiation source and appropriate cooling.

In yet another embodiment, the reaction occurs in a flow reactor equipped with an irradiation source, also named photo-flow reactor.

In one embodiment, the crude reaction can be worked up and the product isolated by standard techniques. In another embodiment, the crude mixture can be further reacted in the next step (reaction step C).

The use of bicyclo[1.1.1]pentane intermediates as prepared by the methods of the invention as key intermediates in many syntheses are as follows (reaction step C):

The intermediate obtained in reaction step B, either purified or crude, is reacted with various nucleophiles.

In one embodiment, X is a leaving group, preferably a halide, more preferably chloride and treatment with an aqueous solution of a base, preferably an inorganic base, provides an acid (when Z=C), a sulfinic acid (when Z=S) or a sulfonic acid (when Z=S(=O)) to afford products of formula Va

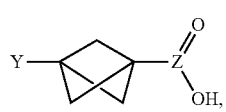

wherein Y, Z are as defined above.

In another embodiment, X is a leaving group, preferably a halide, more preferably chloride and treatment with an alcohol provides an ester (when Z=C), an alkyl sulfinate (when Z=S) or an alkyl sulfonate (when Z=S(=O)) to afford products of formula Vb

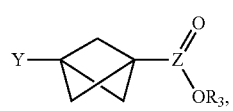

wherein Y, Z, R₁ are as defined above and R₃ is H, saturated linear or branched —(C₁-C₂₀)alkyl, aryl or —N-2-thiopyridone.

In another embodiment, X is a leaving group, preferably a halide, more preferably chloride and treatment with an amine provides an amide (when Z=C), a sulfinamide (when Z=S) or a sulfonamide (when Z=S(=O)) to afford products of formula Vc

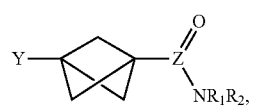

wherein Y, Z, R₁, R₂ are as defined above.

In another embodiment, X is a leaving group, preferably a halide, more preferably chloride, and Z is a C, and treatment with an amino alcohol followed by dehydration gives an oxazolidine or oxazole, or treatment with a diamine followed by dehydration gives an imidazoline or imidazole, or treatment with an amino thiol followed by dehydration gives a thiazole.

In another embodiment, X is an alkyl or aryl and treatment with MCPBA gives an ester.

In another embodiment, X is a halide, preferably chloride, and treatment with an azide salt or ammonia and diphenylphosphorylazide gives access to of Formula Vd.

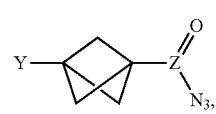

wherein Y, Z are as defined above.

Acyl azides can undergo Curtius rearrangements to afford the corresponding amine or carbamate. Primary amides obtained from treatment with ammonia can undergo Hoffmann rearrangements to provide the corresponding amines In another embodiment, X is a leaving group, preferably a halide, more preferably chloride and Z is C and treatment with diazomethane of formula R₄—CH=N₂ affords diazoketones formula Vh.

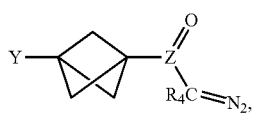

wherein Y, Z, R₄ are as defined above.

Diazoketones can further react in Arndt Eistert rearrangements to afford the homologated acids.

In another embodiment, X is a halide, preferably chloride, and Z is C and treatment with a hydrazine or hydroxylamine affords an acyl hydrazine of Formula Vf or an acyl hydroxylamine of Formula Vg, wherein $R_1$ is H, a saturated linear or branched —$(C_1$-$C_{20})$alkyl, aryl or alkylaryl.

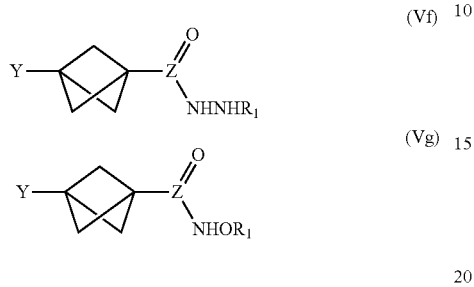

In another embodiment, X is halide, preferably chloride, and Z is C and treatment with a coupling partner, a coupling partner being an alkali metal organyl or an alkaline earth metal organyl ($MR_1$, wherein M is Li, Na or Mg), a stannane ($R_1Sn(R_2)_3$), a cuprate $[R_1CuR_1]^-$ or $[R_1CuCN^-]$) an organozinc compound ($R_1ZnQ$, or $R_1ZnR_1$, wherein Q is halogen), an organobismuth compound (($R_1)_3Bi$), a boronic acid $R_1B(OH)_2$, a boronic ester $R_1B(OR_2)_2$ or a potassium trifluoroborate $R_1BF_3K$ affords a compound of Formula Vi, wherein $R_1$ and $R_2$ are independently of each other-$(C_1$-$C_{20})$ alkyl, aryl or heteroaryl.

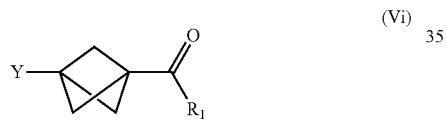

In another embodiment, X is an halide, preferably chloride, and treatment with N-hydroxy-2-thiopyridinone or a similar reagent (i.e. its anion) affords an ester of the type of Barton that provides a terminal bicyclo[1.1.1]pentane after treatment with light or a radical initiator.

In one embodiment, the reaction is run in batch from purified or crude intermediate obtained from reaction step B.

In a preferred embodiment, the desired reactants are added to the same reaction vessel used for reaction step B and the intermediate obtained from reaction step B is used crude (Batch, one-pot reaction sequence).

In another preferred embodiment, the solution of crude intermediate from reaction step B (obtained in batch) is added to a flow system to undergo the next transformation to afford products of formula Va-Vi (Batch->flow sequence).

In another preferred embodiment, the solution of crude intermediate from reaction step B (obtained in flow) is added to a flow system to undergo the next transformation to afford products of formula Va-Vi (flow->flow sequence).

In yet another preferred embodiment, the solution of crude intermediate from reaction step B (obtained in flow) is added to a batch reactor to undergo the next transformation with suitable reactants and afford products of formula Va-Vi (flow->batch sequence).

In another embodiment, the crude or purified intermediate obtained in reaction step B is injected in a flow reaction apparatus to be transformed.

The embodiments discussed herein are merely illustrative and are not meant to limit the scope of the present invention.

EXAMPLES

Example 1: 3-(chlorocarbonyl)bicyclo[1.1.1]pentane-1-carboxylates in Batch Conditions (a) Methyl 3-(chlorocarbonyl)bicyclo[1.1.1]pentane-1-carboxylate (4) Prepared in Batch Conditions

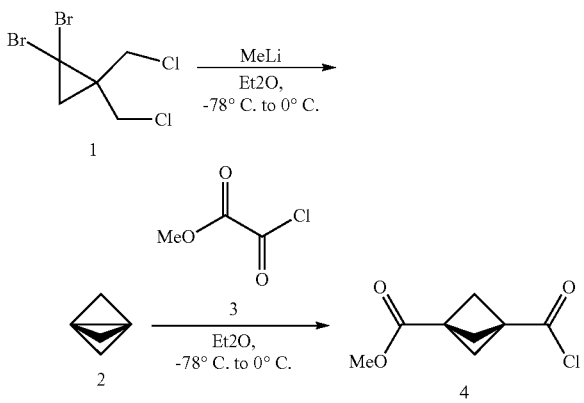

(i) [1.1.1]propellane 2

To a suspension of 1,1-dibromo-2,2-bis(chloromethyl)cyclopropane (1, 518 g, 1.74 mol, 1 equiv.) in dry $Et_2O$ (600 mL) was added dropwise by cannula a 1.6 M MeLi solution in $Et_2O$ (2400 mL, 3.83 mol, 2.2 equiv.) at −50 to −60° C. under $N_2$ atmosphere. After MeLi addition, the reaction mixture was allowed to warm to 0° C. over 1 h. Then, the reaction mixture was removed from the dry ice/acetone bath and placed in an ice-water bath at 0° C. and stirred for 2 h. Then, a distillation apparatus is connected and the receiving flask is cooled to −78° C. [1.1.1]propellane 2 is obtained as a solution in $Et_2O$ in a concentration of 0.3 to 0.6 M in 70-95% yield.

(ii) Methyl 3-(chlorocarbonyl)bicyclo[1.1.1]pentane-1-carboxylate (4)

To a distilled solution of [1.1.1]propellane in $Et_2O$ (750 mL, 375 mmol, 1 equiv) between −20 and −30° C. was added methyl 2-chloro-2-oxoacetate 3 (41.9 mL, 375 mmol, 1 equiv.). The reaction mixture was irradiated using a Hanovia medium pressure mercury-vapor lamp until full consumption of [1.1.1]propellane, giving methyl 3-(chlorocarbonyl)bicyclo[1.1.1]pentane-1-carboxylate 4 in $Et_2O$ solution. This solution can be used directly without further purification with a nucleophile to obtain another bicyclo[1.1.1]pentane derivative or the solvent can be removed under reduced pressure to obtain methyl 3-(chlorocarbonyl)bicyclo[1.1.1]pentane-1-carboxylate 4 as a yellow solid which can be used for any other suitable step without further purification.

(b) Ethyl 3-(chlorocarbonyl)bicyclo[1.1.1]pentane-1-carboxylate (6) Prepared in Batch Conditions

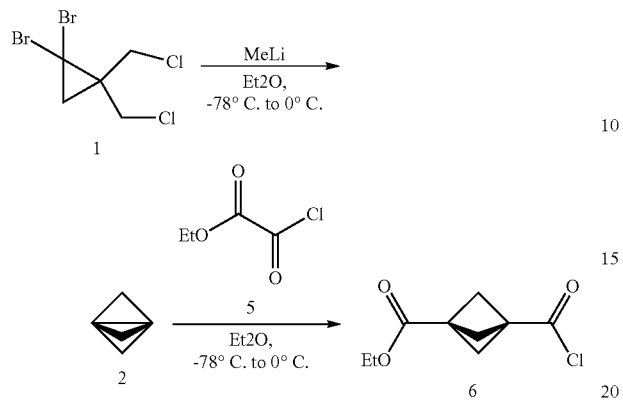

To a distilled solution of [1.1.1]propellane in Et$_2$O 2, prepared as described in example 1(a) (750 mL, 305 mmol, 1 equiv.) between −20 and −30° C. was added ethyl chlorooxoacetate 5 (34.1 mL, 305 mmol, 1 equiv.). The reaction mixture was irradiated with a Hanovia medium pressure mercury-vapor lamp until full consumption of [1.1.1]propellane, giving ethyl 3-(chlorocarbonyl)bicyclo[1.1.1]pentane-1-carboxylate 6 in an etheral solution. This solution can be used directly without further purification with a nucleophile to obtain another bicyclo[1.1.1]pentane derivative or the solvent can be removed under reduced pressure to obtain ethyl 3-(chlorocarbonyl)bicyclo[1.1.1]pentane-1-carboxylate 6 as a yellow solid which can be used for any other suitable step without further purification.

(c) tert-Butyl 3-(chlorocarbonyl)bicyclo[1.1.1]pentane-1-carboxylate (8) Prepared in Batch Conditions

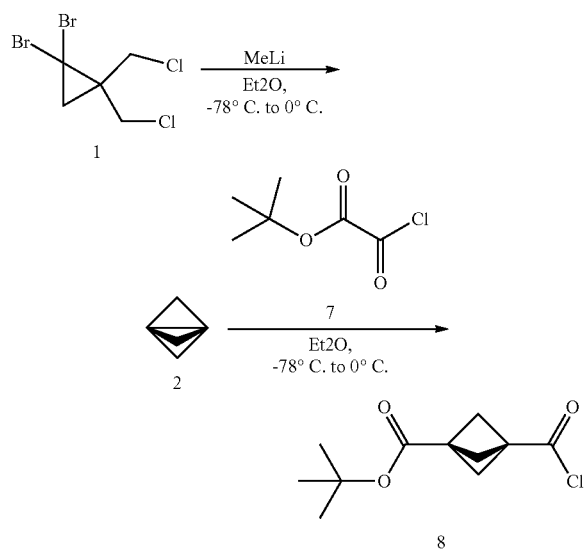

To a distilled solution of [1.1.1]propellane in Et$_2$O 2, prepared as described in example 1(a) (333 mL, 136 mmol, 1 equiv.) between −20 and −30° C. was added tert-butyl 2-chloro-2-oxoacetate 7 (22.38 g, 136 mmol, 1 equiv.). The reaction mixture was irradiated with a Hanovia medium pressure mercury-vapor lamp until full consumption of [1.1.1]propellane, giving tert-butyl 3-(chlorocarbonyl)bicyclo[1.1.1]pentane-1-carboxylate 8 in an etheral solution. This solution can be used directly without further purification with a nucleophile to obtain another bicyclo[1.1.1]pentane derivative or the solvent can be removed under reduced pressure to obtain tert-butyl 3-(chlorocarbonyl)bicyclo[1.1.1]pentane-1-carboxylate 8 which can be used for any other suitable step without further purification.

Example 2: 3-(alkyloxycarbonyl)bicyclo[1.1.1]pentane-1-carboxylic Acids Prepared in Batch Conditions (a) 3-(Methoxycarbonyl)bicyclo[1.1.1]pentane-1-carboxylic Acid 9 Prepared in Batch Conditions

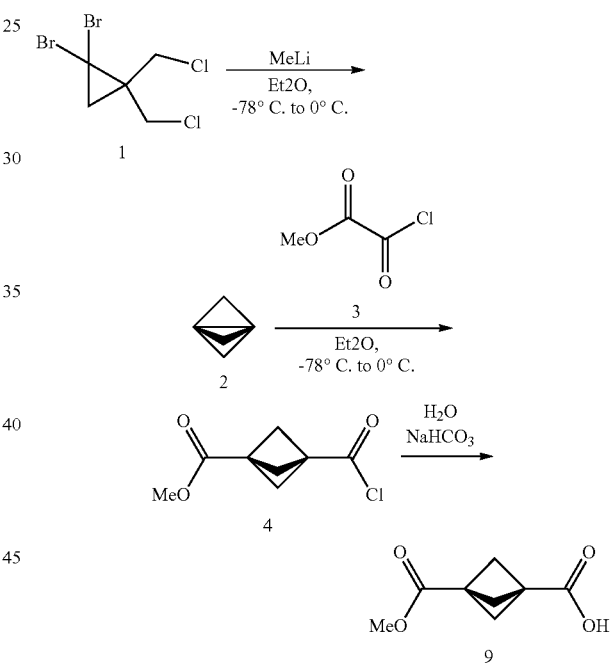

To a solution of methyl 3-(chlorocarbonyl)bicyclo[1.1.1]pentane-1-carboxylate 4 in Et$_2$O prepared as described in example 1(a) was added 1 L of distilled water and a solid inorganic base or an aqueous basic solution such as NaOH, KOH, NaHCO$_3$, KHCO$_3$, etc until the pH was basic and the mixture was vigorously stirred at rt between 2 and 16 h. The aqueous layer was separated and extracted with DCM (×2). Then the aqueous phase was acidified to pH=1. This mixture was extracted with DCM (×3) and the combined organic layers were dried over anhydrous MgSO$_4$, filtered and concentrated under reduced pressure to provide 3-(methoxycarbonyl)bicyclo[1.1.1]pentane-1-carboxylic acid 9 in 30% yield as a pale yellow solid. 1H NMR: (400 MHz, Chloroform-d) δ 3.69 (s, 3H), 2.40 (s, 6H) ppm. 13C NMR: (400 MHz, Chloroform-d) δ 174.86, 169.56, 52.80, 51.90, 37.55 ppm.

(b) 3-(ethoxycarbonyl)bicyclo[1.1.1]pentane-1-carboxylic Acid 10 Prepared in Batch Conditions

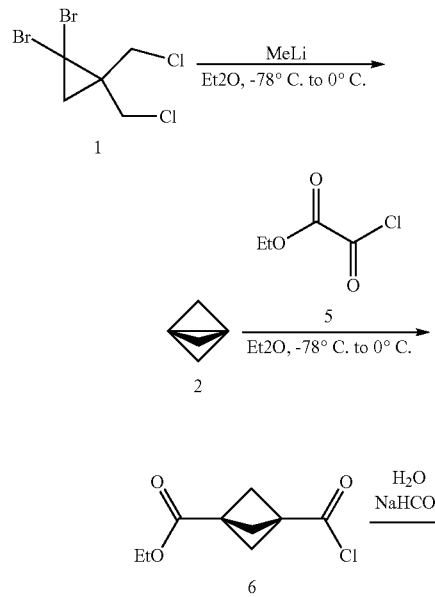

To a solution of ethyl 3-(chlorocarbonyl)bicyclo[1.1.1]pentane-1-carboxylate 6 in Et₂O prepared as described in example 1(b) was added 1 L of distilled water and a solid inorganic base or an aqueous basic solution such as NaOH, KOH, NaHCO₃, KHCO₃, etc until the pH was basic and the mixture was vigorously stirred at rt between 2 and 16 h. The aqueous layer was separated and extracted with DCM (×2). Then the aqueous phase was acidified to pH=1. This mixture was extracted with DCM (×3) and the combined organic layers were dried over anhydrous MgSO₄, filtered and concentrated under reduced pressure to provide 3-(ethoxycarbonyl)bicyclo[1.1.1]pentane-1-carboxylic acid 10 in 42% yield as a white solid. 1H NMR: (400 MHz, Chloroform-d) δ 1.27 (t, J=7.2 Hz, 3H), 2.34 (s, 6H), 4.14 (q, J=7.2 Hz, 2H), 10.65 (bs, 1H). 13C NMR: (400 MHz, Chloroform-d) δ 175.1, 169.5, 61.0, 52.8, 37.8, 37.5, 14.2 ppm.

(c) 3-(tert-butyloxycarbonyl)bicyclo[1.1.1]pentane-1-carboxylic Acid 11 Prepared in Batch Conditions

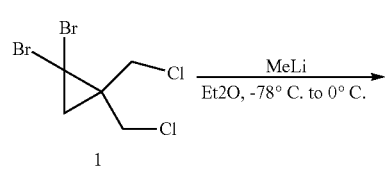

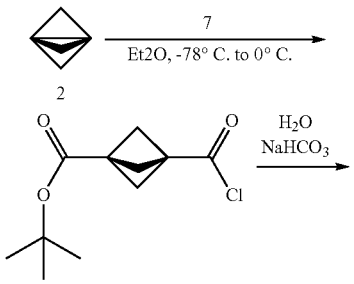

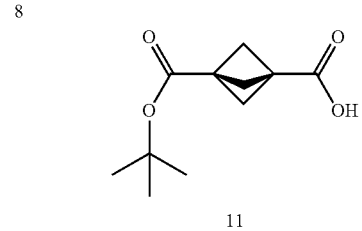

To a solution of tert-butyl 3-(chlorocarbonyl)bicyclo[1.1.1]pentane-1-carboxylate 8 in Et₂O prepared as described in example 1(c) was added 1 L of distilled water and a solid inorganic base or an aqueous basic solution such as NaOH, KOH, NaHCO₃, KHCO₃, etc until the pH was basic and the mixture was vigorously stirred at rt between 2 and 16 h. The aqueous layer was separated and extracted with DCM (×2). Then the aqueous phase was acidified to pH=1. This mixture was extracted with DCM (×3) and the combined organic layers were dried over anhydrous MgSO₄, filtered and concentrated under reduced pressure to provide 3-(tert-butoxycarbonyl)bicyclo[1.1.1]pentane-1-carboxylic acid 11 in 24% yield. 1H NMR: (400 MHz, Chloroform-d) δ 2.28 (s, 6H), 1.56 (s, 9H).

Example 3 3-(alkyloxycarbonyl)bicyclo[1.1.1]pentane-1-carboxylic Acids and alkyl 3-(halocarbonyl)bicycle[1.1.1]pentane-1-carboxylates Prepared in Flow Conditions (a) 3-(methoxycarbonyl)bicyclo[1.1.1]pentane-1-carboxylic Acid (9) Using Flow System

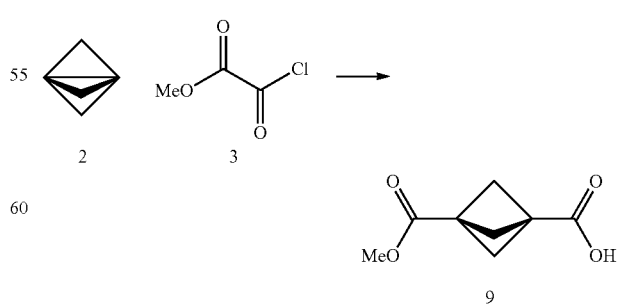

A solution of [1.1.1]propellane in Et₂O 2 (500 mL, 161 mmol, 1 equiv.), and a solution of methyl chlorooxoacetate 3 (16.3 mL, 177 mmol, 1.1 equiv.) in Et$_2$O (49.7 mL) were prepared independently. The entire reactor was flushed with pure Et$_2$O (pump 1: 4.0 mL·min$^{-1}$, pump 2: 0.5 mL·min$^{-1}$) for 5 min. The solution of reagent (2) at 0 to −80° C. was then injected at a flow rate of 4.0 mL·min$^{-1}$ and the solution of reagent (3) at room temperature was then injected at a flow rate of 0.5 mL·min$^{-1}$ to the photoreactor (volume 58 mL; FEP tube was rotated on the lamp) in an ice bath. The reaction mixture was quenched with aqueous basic solution of NaOH, KOH, NaHCO3 or KHCO3, etc after the solution exits the photoreactor. After 2 h of vigorous stirring, the aqueous layer was separated and acidified until pH=1. The mixture was then extracted with DCM (3×500 mL). The combined organic layers were dried over MgSO$_4$, filtered and concentrated under reduced pressure to provide 3-(methoxycarbonyl)bicyclo[1.1.1]pentane-1-carboxylic acid (9, 17.5 g, 103 mmol, 63%) as a pale yellow solid.

(b) 3-(ethoxycarbonyl)bicyclo[1.1.1]pentane-1-carboxylic Acid 10 Using a Flow System

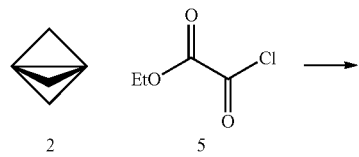

2  5

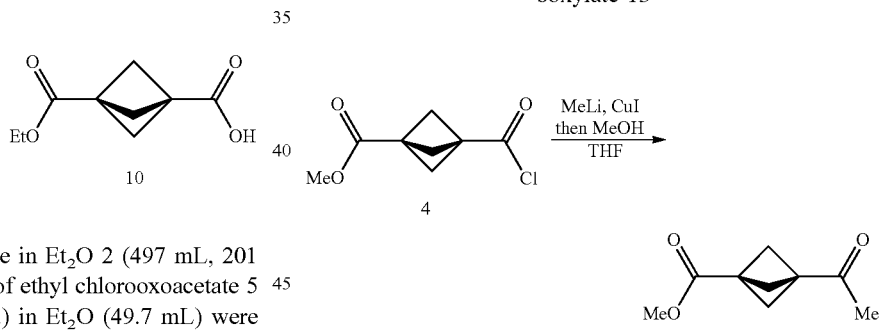

10

A solution of [1.1.1]propellane in Et$_2$O 2 (497 mL, 201 mmol, 1 equiv.), and a solution of ethyl chlorooxoacetate 5 (20.2 mL, 181 mmol, 0.9 equiv.) in Et$_2$O (49.7 mL) were prepared independently. The entire reactor was flushed with pure Et$_2$O (HPLC pump 1: 9.0 mL·min-1, HPLC pump 2: 0.9 mL·min-1) for 5 min. The solution of reagent (2) at −50 to −60° C. was then injected at a flow rate of 9.0 mL·min-1 and the solution of reagent (5) at room temperature was then injected at a flow rate of 0.9 mL·min$^{-1}$ to the photoreactor (volume 58 mL; FEP tube was rotated on the lamp) in an ice bath. After 1 h, the reaction mixture was quenched with aqueous basic solution of NaOH, KOH, NaHCO$_3$ or KHCO3, etc after the solution exits the photoreactor and the solution was vigorously stirred over 30 min, then, the aqueous layer and the organic layer were separated. The aqueous layer was acidified until pH=1. The mixture was then extracted with DCM (3×500 mL). The combined organic layers were dried over MgSO$_4$, filtered and concentrated under reduced pressure to provide 3-(ethoxycarbonyl) bicyclo[1.1.1]pentane-1-carboxylic acid 10 (18.2 g, 98.8 mmol, 49%) as a pale yellow solid.

Example 4: Preparation of Compounds of Formula (V)

(a) Ethyl 3-(dimethylcarbamoyl)bicyclo[1.1.1]pentane-1-carboxylate 12

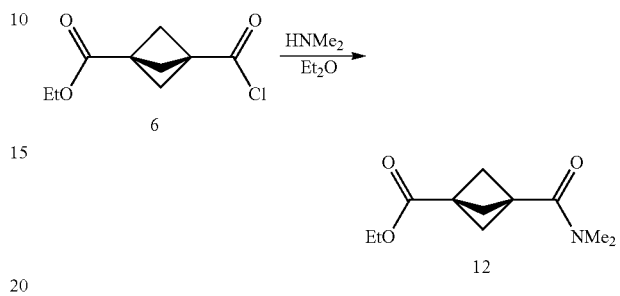

To a solution of ethyl 3-(chlorocarbonyl)bicyclo[1.1.1]pentane-1-carboxylate 6 (1.17 g, 5.81 mmol, 1 equiv.) in diethyl ether was added dropwise dimethylamine (2.91 mL, 5.81 mmol, 1 equiv.) at rt and the mixture was stirred 2 h. Then, water was added and the crude was extracted with EtOAc. The combined organic layer was dried over anhydrous MgSO$_4$, filtered and the volatiles removed under reduced pressure to provide ethyl 3-(dimethylcarbamoyl) bicyclo[1.1.1]pentane-1-carboxylate 12.

(b) Methyl 3-acetylbicyclo[1.1.1]pentane-1-carboxylate 13

To a suspension of CuI (2.52 g, 13.23 mmol, 1.2 equiv.) in dry THF (30.6 mL), was added MeLi 1.6 M in Et$_2$O (16.5 mL, 26.5 mmol, 2.4 equiv.) dropwise at 0° C. under N$_2$ atmosphere. Then, the reaction mixture was cooled down to −78° C. and a solution of methyl 3-(chlorocarbonyl)bicyclo[1.1.1]pentane-1-carboxylate 4 in dry THF (30.6 mL) was added dropwise. The reaction mixture was stirred at −78° C. for 2 h and then, methanol (11.15 mL, 276 mmol, 25 equiv.) was added and the mixture was allowed to warm to rt. A saturated solution of NH$_4$Cl was added and the mixture extracted with EtOAc (×3). The combined organic layers were dried over anhydrous MgSO$_4$, filtered and concentrated in vacuum. The residue was purified by flash chromatography (EtOAc/hexanes 0% to 75%) to provide methyl 3-acetylbicyclo[1.1.1]pentane-1-carboxylate 13 as an oil in 49% yield. 1H NMR: (400 MHz, Chloroform-d) δ 3.69 (s, 3H), 2.28 (s, 6H), 2.09 (s, 3H) ppm.

(c) Ethyl 3-carbamoylbicyclo[1.1.1]pentane-1-carboxylate 14

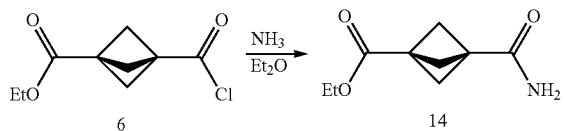

To a solution of ethyl 3-(chlorocarbonyl)bicyclo[1.1.1]pentane-1-carboxylate 6 (1.17 g, 5.81 mmol, 1 equiv.) in diethyl ether was added dropwise 7M ammonia in methanol (0.8 mL, 5.6 mmol, 1 equiv.) at rt and the mixture was stirred 2 h. Then, water was added and the crude was extracted with EtOAc. The combined organic layer was dried over anhydrous MgSO$_4$, filtered and the volatiles removed under reduced pressure to provide ethyl 3-carbamoylbicyclo[1.1.1]pentane-1-carboxylate 14.

(d) Ethyl bicyclo[1.1.1]pentane-1-carboxylate 15

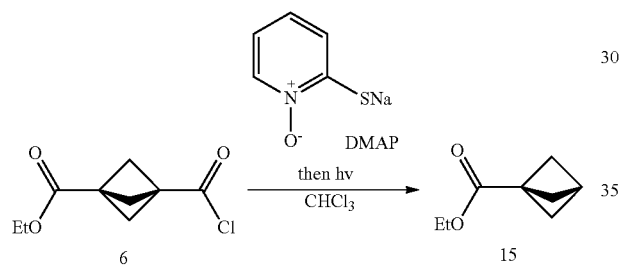

A solution of ethyl 3-(chlorocarbonyl)bicyclo[1.1.1]pentane-1-carboxylate 6 (26.99 g, 143 mmol) in chloroform (100 ml) was added dropwise to a mixture of sodium 2-sulfidopyridine 1-oxide (21.34 g, 143 mmol, 1 equiv.) and N,N-dimethylpyridin-4-amine (1.748 g, 14.31 mmol, 0.1 equiv.) in chloroform (700 ml) at 23° C. under N$_2$ atmosphere and the mixture was stirred for 30 min. Then, the mixture was irradiated with a tungsten lamp (240 W) for 2 h. The crude was washed with 1M HCl, sat. NaHCO$_3$, brine, dried over anhydrous MgSO$_4$, filtered through a silica pad and concentrated in vacuum to obtain methyl bicyclo[1.1.1]pentane-1-carboxylate as a colorless oil in 36% yield. 1H NMR (300 MHz, CDCl3) δ 3.66 (3H), 2.42 (1H), 2.08 (6H).

(e) ethyl 3-(methoxy(methyl)carbamoyl)bicyclo[1.1.1]pentane-1-carboxylate 16

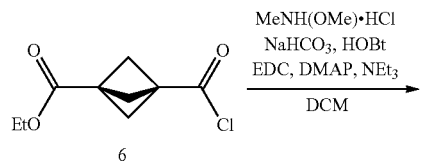

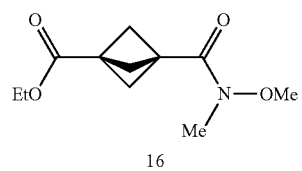

Ethyl 3-(chlorocarbonyl)bicyclo[1.1.1]pentane-1-carboxylate 6 (4.7 g, 23 mmol) was dissolved in Et$_2$O was added NaHCO$_3$ (1 equiv.) and the mixture was stirred for 2 h. Then, the crude was diluted with water and extracted with DCM (×2) the aqueous phase was acidified with 6M HCl solution to pH=1 and extracted again with DCM (×3). The volatiles were dried over anhydrous MgSO$_4$ and evaporated under reduced pressure. The residue was re-suspended in DCM (503 mL) and a catalytic amount of HOBt and DMAP, N,O-dimethylhydroxylamine (4.90 g) and EDC (9.3 g) were added and the mixture was stirred at rt overnight. Then, the reaction mixture was poured into water and extracted with EtOAc. The combined organic layers were washed with brine, dried over anhydrous MgSO$_4$, filtered and concentrated in vacuum. The residue was purified by flash chromatography (EtOAc/hex 0% to 80%) to obtain ethyl 3-(methoxy(methyl)carbamoyl)bicyclo[1.1.1]pentane-1-carboxylate 16 in 46% yield.

(f) ethyl 3-(2-diazoacetyl)bicyclo[1.1.1]pentane-1-carboxylate 17

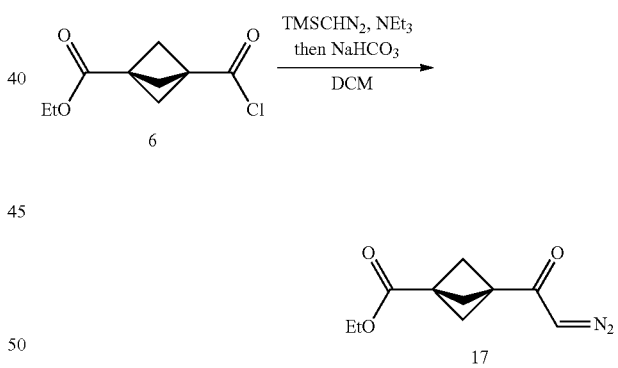

Ethyl 3-(chlorocarbonyl)bicyclo[1.1.1]pentane-1-carboxylate 6 (1.1 g, 5.4 mmol) was dissolved in a MeCN (13 mL) and THF (13 mL) mixture and added dropwise to an ice water cooled solution of (diazomethyl)trimethylsilane (2.71 mL, 5.43 mmol) and triethylamine (1.13 mL, 8.15 mmol) in a MeCN (13 mL) and THF (13 mL) mixture and the reaction was allowed to warm to rt and stirred overnight. Then, the solvents were removed and the residue re-dissolved in EtOAc and washed with water, sat. NaHCO$_3$ solution and brine. The organic layer was dried over anhydrous MgSO$_4$, filtered and concentrated in vacuum. The crude was purified by flash chromatography with (EtOAc/hexanes 20% to 50%) to provide ethyl 3-(2-diazoacetyl)bicyclo[1.1.1]pentane-1-carboxylate 17 in 56% yield as a yellow oil.

(g) ethyl 3-(4,4-dimethyl-4,5-dihydrooxazol-2-yl) bicyclo[1.1.1]pentane-1-carboxylate 18

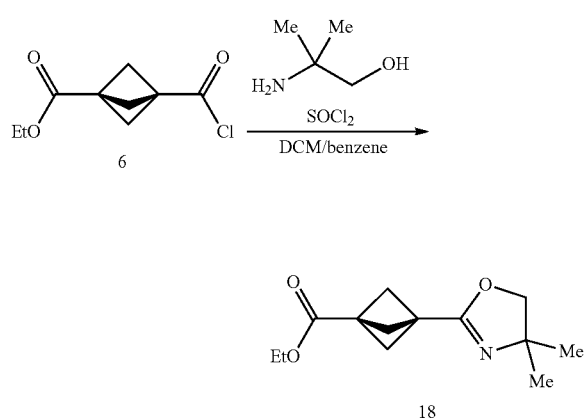

To a solution of ethyl 3-(chlorocarbonyl)bicyclo[1.1.1]pentane-1-carboxylate 6 in DCM was added 5 equiv. of 2-amino-2-methylpropan-1-ol at 0° C. and the reaction mixture was allowed to warm to rt and stirred overnight. Then the reaction was diluted with DCM, washed with water (×3), 1M HCl solution, brine, dried over anhydrous $MgSO_4$, filtered and concentrated in vacuum. The residue was resuspendend in a DCM/benzene (5:2) mixture and thionyl chloride (3 equiv) was added at rt and the mixture refluxed briefly and stirred at rt for 3 h. Then, the reaction mixture was frozen with liquid $N_2$ and $Et_2O$ followed by 10 M NaOH solution addition. The liquid $N_2$ bath was removed and water was added. The mixture was allowed to warm up to rt, diluted with $Et_2O$, washed with water and brine, dried over $MgSO_4$, filtered and concentrated in vacuum to provide ethyl 3-(4,4-dimethyl-4,5-dihydrooxazol-2-yl)bicyclo[1.1.1]pentane-1-carboxylate 18 in 56% yield.

(h) ethyl 3-(hydroxymethyl)bicyclo[1.1.1]pentane-1-carboxylate 19

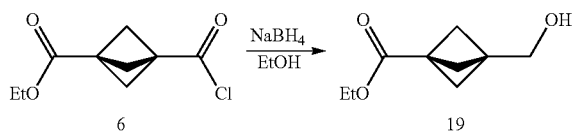

To a solution of ethyl 3-(chlorocarbonyl)bicyclo[1.1.1]pentane-1-carboxylate 6 (1.135 g, 5.6 mmol, 1 equiv.) in EtOH (20 mL) was added $NaBH_4$ (0.636 g, 16.8 mmol, 3 equiv) and the reaction was stirred at rt overnight. Then, the mixture was quenched with water and extracted with EtOAc (×3), the combined organic layers were dried over $MgSO_4$, filtered and concentrated in vacuum to provide ethyl 3-(hydroxymethyl)bicyclo[1.1.1]pentane-1-carboxylate 19.

(i) ethyl 3-((3-bromobenzyl)carbamoyl)bicyclo[1.1.1]pentane-1-carboxylate 20

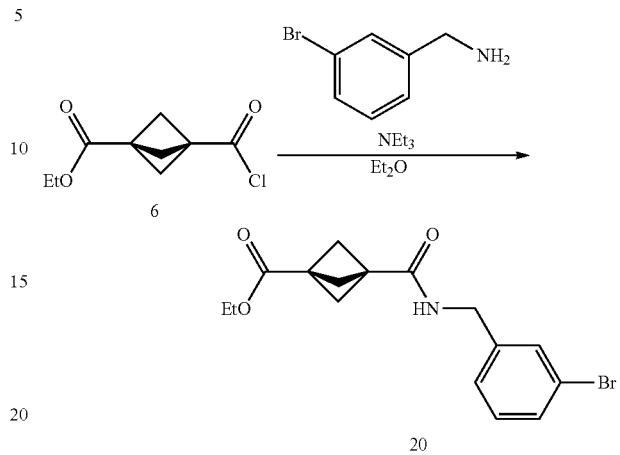

To a solution of ethyl 3-(chlorocarbonyl)bicyclo[1.1.1]pentane-1-carboxylate 6 (1.13 g, 5.6 mmol, 1 equiv.) in $Et_2O$ was added dropwise (3-bromophenyl)methanamine (1.04 g, 5.6 mmol, 1 equiv.) at rt and the mixture was stirred 2 h. Then, water was added and the crude was extracted with EtOAc. The combined organic layers were dried over $MgSO_4$, filtered and the volatiles removed under reduced pressure to provide ethyl 3-((3-bromobenzyl)carbamoyl)bicyclo[1.1.1]pentane-1-carboxylate 20.

(j) ethyl 3-(3-aminobenzoyl)bicyclo[1.1.1]pentane-1-carboxylate 21

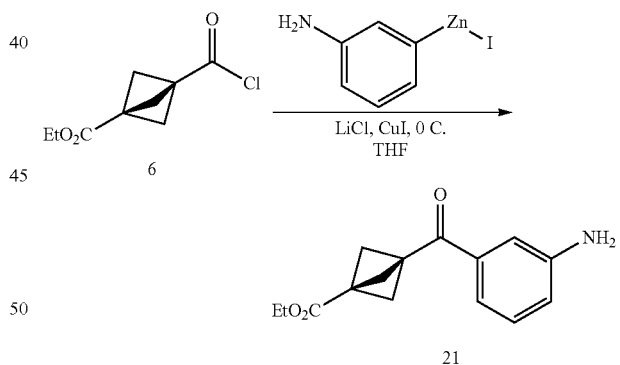

3-aminophenylzinc iodide (4 mL, 0.25M in THF, 1 mmol) was added to a round bottom flask under $N_2$ atmosphere and cooled to OC in an ice-bath. Then, ethyl 3-(chlorocarbonyl)bicyclo[1.1.1]pentane-1-carboxylate 6 (161 mg, 0.8 mmol) was added and the mixture was allowed to warm to rt and stirred for 3 h at rt. Then, the mixture was quenched with sat. $NH_4Cl$ solution and extracted with EtOAc (×3). The combined organic layers were washed with sat. $NaHCO_3$ solution, 8% $NH_4OH$ solution and brine and dried over anhydrous $MgSO_4$, filtered and concentrated in vacuum. Ethyl 3-(3-aminobenzoyl)bicyclo[1.1.1]pentane-1-carboxylate 21 was obtained by crystallization from hexane/$Et_2O$.

(k) Ethyl 3-(4-(ethoxycarbonyl)benzoyl)bicyclo[1.1.1]pentane-1-carboxylate 22

(m) Ethyl 3-benzoylbicyclo[1.1.1]pentane-1-carboxylate 24

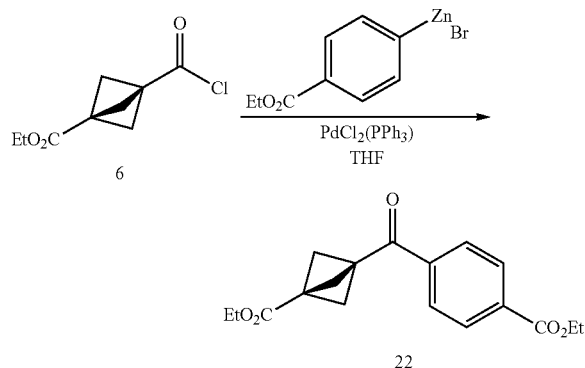

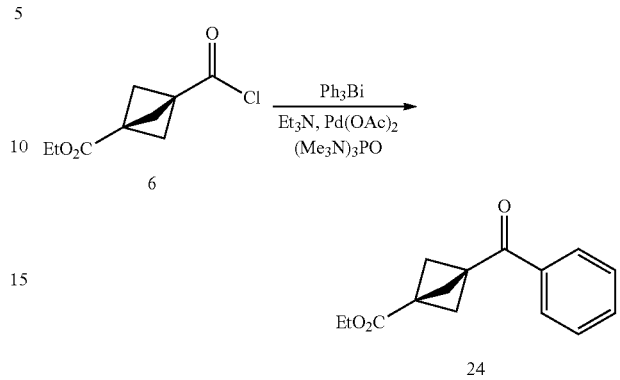

Ethyl 3-(chlorocarbonyl)bicyclo[1.1.1]pentane-1-carboxylate 6 (1.05 g, 5.2 mmol) and PdCl$_2$(PPh$_3$) (1760 mg, 0.25 mmol) were dissolved in THF (35 mL). Then, (4-(ethoxycarbonyl)phenyl)zinc(II) bromide 0.5 M solution in THF (10 mL, 5 mmol) was added at rt and the mixture was stirred at the same temperature for 5 h. Then, the mixture was partitioned between Et$_2$O and sat. NH$_4$Cl and the aqueous phase extracted with Et$_2$O. The combined organic layers were washed with brine, dried over anhydrous MgSO$_4$, filtered and concentrated in vacuum. The crude was purified by flash chromatography with EtOAc/hexanes from 0% to 10% to obtain Ethyl 3-(4-(ethoxycarbonyl)benzoyl)bicyclo[1.1.1]pentane-1-carboxylate 22.

Pd(OAc)$_2$ (0.05 mmol) was suspended in HMPA (1 mL) under N$_2$ atmosphere at rt. Et$_3$N (134 uL, 0.1 mmol) was added and the mixture was stirred for 5 min. Then, a solution of ethyl 3-(chlorocarbonyl)bicyclo[1.1.1]pentane-1-carboxylate 6 (1.05 g, 5.2 mmol) in HMPA (3 mL) was added dropwise, followed by addition of triphenylbismuth (1 mmol) in HMPA (5 mL). The crude was heated at 65° C. for 5 h. Then, the crude was allowed to cool down to rt and diluted with Et$_2$O, filtered through basic alumina and washed with Et$_2$O. The ethereal solution was washed with water, dried over anhydrous MgSO4, filtered and concentrated in vacuum. The residue was purified by flash chromatography with EtOAc/hexanes from 0% to 20% to provide ethyl 3-benzoylbicyclo[1.1.1]pentane-1-carboxylate 24

(l) Ethyl 3-(3-methylbenzoyl)bicyclo[1.1.1]pentane-1-carboxylate 23

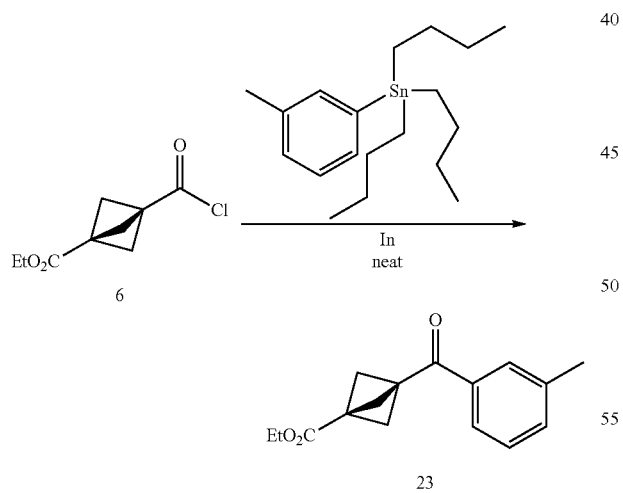

Ethyl 3-(chlorocarbonyl)bicyclo[1.1.1]pentane-1-carboxylate 6 (1.05 g, 5.2 mmol) and tributyl(m-tolyl)stannane previously prepared (0.99 g, 2.6 mmol, 0.5 equiv.) and Indium metal (0.6 g, 1 equiv) were mixed in neat conditions and stirred for 25 h. Then, the crude was purified by flash chromatography with EtOAc/Hexanes from 0% to 20% to obtain Ethyl 3-(3-methylbenzoyl)bicyclo[1.1.1]pentane-1-carboxylate 23.

The invention claimed is:

1. A one-step process for producing an asymmetrically substituted compound of formula I,

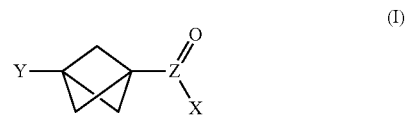

comprising the step of reacting [1.1.1]propellane of formula II

with a compound of formula III, wherein

Z is C, S or S(=O);
Y is R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—,

R$_1$SC(=O)—, R$_1$R$_2$N—, —NO$_2$, or —CH(=NOR$_1$), wherein R$_1$ and R$_2$ are independently of each other H, saturated linear or branched —(C$_1$-C$_{20}$)alkyl, or aryl or R$_1$ and R$_2$ form together a cycle; and X is halogen, —OR$_1$, or —NR$_1$R$_2$, wherein R$_1$ and R$_2$ are independently of each other H, saturated linear or branched —(C$_1$-C$_{20}$)alkyl, or aryl or R$_1$ and R$_2$ form together a cycle.

2. The one-step process according to claim 1, wherein X is halogen.

3. The one-step process according to claim 2, further comprising the step of reacting the obtained compound of formula I with a nucleophile, selected from HOR$_1$, HSR$_1$, HNR$_1$R$_2$, —N$_3$, H$_3$N, H$_2$N—NHR$_1$, H$_2$N—OR$_1$, R$_4$CH(=N$_2$), or N-hydroxy-2-thiopyridone or with coupling partner, a coupling partner being an alkali metal organyl or an alkaline earth metal organyl of the following formula MR$_1$, wherein M is Li, Na or Mg, a stannane of the following formula R$_1$Sn(R$_2$)$_3$, a cuprate of the following formula [R$_1$CuR$_1$]$^-$ or [R$_1$CuCN$^-$], an organozinc compound of the following formula R$_1$ZnQ, or R$_1$ZnR$_1$, wherein Q is halogen, an organobismuth compound of the following formula (R$_1$)$_3$Bi, a boronic acid of the following formula R$_1$B(OH)$_2$, a boronic ester of the following formula R$_1$B(OR$_2$)$_2$ or a potassium trifluoroborate of the following formula R$_1$BF$_3$K, wherein R$_1$ and R$_2$ are independently of each other H, saturated linear or branched —(C$_1$-C$_{20}$)alkyl, or aryl or R$_1$ and R$_2$ form together a cycle and R$_4$ represents H, saturated or unsaturated linear or branched —(C$_1$-C$_{20}$)alkyl, trimethylsilvl (TMS), or aryl to obtain a compound of formula V

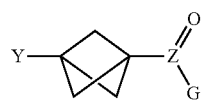
(V)

wherein
Z is C, S or S(=O);
Y is R$_1$—C(=O)—, R$_1$OC(=O)—, CH$_2$F—, CHF$_2$—, CF$_3$—, C$_2$F$_5$—, C$_3$F$_7$—, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, or aryl or R$_1$ and R$_2$ form together a cycle; and
G is —OR$_1$, —SR$_1$, —NR$_1$R$_2$, —N$_3$, —NH$_2$—NH—NHR$_1$, —NH—OR$_1$, —C(=N$_2$) R$_4$, —O—(N-2-thiopyridone), or R$_1$, wherein R$_1$ and R$_2$ are independently of each other H, saturated linear or branched —(C$_1$-C$_{20}$)alkyl, or aryl, or R$_1$ and R$_2$ form together a cycle and R$_4$ represents H, saturated or unsaturated linear or branched —(C$_1$-C$_{20}$)alkyl, TMS, or aryl.

4. The one-step process according to claim 1 wherein the [1.1.1]propellane of formula II is obtained by reaction of a tetrahalide of formula IV with an alkyl or aryl lithium at temperature below 0° C.

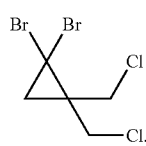
(IV)

5. The process according to claim 3, wherein the reaction steps to obtain a compound of formula V from a compound of formula II are performed (a) in a batch system and/or (b) in a flow system.

6. The process according to claim 4, wherein the reaction steps to obtain a compound of formula I from a compound of formula IV are performed (a) in a batch system and/or (b) in a flow system.

7. The process according to claim 3 wherein the [1.1.1] propellane of formula II is obtained by reaction of a tetrahalide of formula IV with an alkyl or aryl lithium at temperature below 0° C.

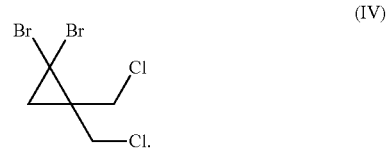
(IV)

8. The one-step process according to claim 1 wherein the step of reacting [1.1.1]propellane of formula II with a compound of formula III is carried out under irradiation.

9. The one-step process according to claim 1 wherein the step of reacting [1.1.1]propellane of formula II with a compound of formula III is carried out in the presence of a radical initiator.

10. The process according to claim 3 wherein the compound of formula I is reacted with a nucleophile and the nucleophile comprises water to obtain products of formula Va, wherein

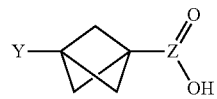
(Va)

Z is C, S or S(=O); and
Y is R$_1$—C(=O)—, R$_1$OC(=O)—, —CH$_2$F, —CHF$_2$, —CF$_3$, —C$_2$F$_5$, —C$_3$F$_7$, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, or aryl, or R$_1$ and R$_2$ form together a cycle.

11. The process according to claim 3 wherein the compound of formula I is reacted with a nucleophile and the nucleophile is HOR$_1$ or N-hydroxy-2-thiopyridone to obtain a compound of formula Vb, wherein

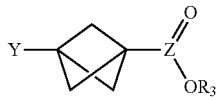
(Vb)

Z is C, S or S(=O);
Y is R$_1$—C(=O)—, R$_1$OC(=O)—, CH$_2$F—, CHF$_2$—, CF$_3$—, C$_2$F$_5$—, C$_3$F$_7$—, —CN, R$_1$R$_2$NC(=O)—, R$_1$SC(=O)—, R$_1$R$_2$N—, —NO$_2$, or —CH(=NOR$_1$), wherein R$_1$ and R$_2$ are independently of each other H, saturated linear or branched —(C$_1$-C$_{20}$)alkyl, or aryl or R$_1$ and R$_2$ form together a cycle; and R$_3$ is H, saturated linear or branched —(C$_1$-C$_{20}$)alkyl, aryl or —N-2-thiopyridone.

12. The process according to claim 3 wherein the compound of formula I is reacted with a nucleophile and the nucleophile is HNR$_1$R$_2$ to obtain compounds of formula (Vc), wherein

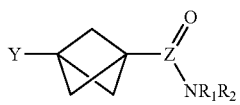

(Vc)

Z is C, S or S(=O);
Y is R$_1$—C(=O)—, R$_1$OC(=O)—, CH$_2$F—, CHF$_2$—, CF$_3$—, C$_2$F$_5$—, C$_3$F$_7$—, —CN, R$_1$R$_2$NC(=O)—, R$_1$SC(=O)—, R$_1$R$_2$N—, —NO$_2$, or —CH(=NOR$_1$); and
R$_1$ and R$_2$ are independently of each other H, saturated linear or branched —(C$_1$-C$_{20}$)alkyl, or aryl or R$_1$ and R$_2$ form together a cycle.

13. The process according to claim 3 wherein the compound of formula I is reacted with a nucleophile and the nucleophile is $^-$N$_3$, H$_3$N, H$_2$N—NHR$_1$, H$_2$N—OR$_1$, or R$_4$CH(=N$_2$), to form products of formulae Vd-h, wherein

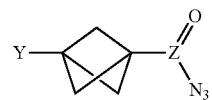

(Vd)

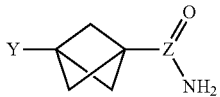

(Ve)

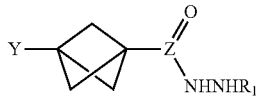

(Vf)

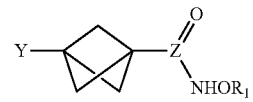

(Vg)

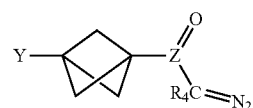

(Vh)

Z is C, S or S(=O);
Y is R$_1$—C(=O)—, R$_1$OC(=O)—, CH$_2$F—, CHF$_2$—, CF$_3$—, C$_2$F$_5$—, C$_3$F$_7$—, —CN, R$_1$R$_2$NC(=O)—, R$_1$SC(=O)—, R$_1$R$_2$N—, —NO$_2$, —CH(=NOR$_1$), wherein R$_1$ and R$_2$ are independently of each other H, saturated linear or branched —(C$_1$-C$_{20}$)alkyl, or aryl or R$_1$ and R$_2$ form together a cycle;
R$_4$ is H, saturated or unsaturated linear or branched —(C$_1$-C$_{20}$)alkyl, TMS, or aryl.

14. The one-step process according to claim 1 wherein Z is C.

15. The one-step process according to claim 1 wherein Z is S.

16. The one-step process according to claim 1 wherein Z is S(=O).

17. The one-step process according to claim 1, wherein Y represents R$_1$—C(=O)— or R$_1$OC(=O)—, and R$_1$ is saturated linear or branched —(C$_1$-C$_{20}$)alkyl or aryl.

18. The process according to claim 10 wherein the nucleophile is an aqueous solution of an organic or inorganic base.

19. The process according to claim 7, wherein the reaction steps to obtain a compound of formula V from a compound of formula IV are performed (a) in a batch system and/or (b) in a flow system.

* * * * *